(12) United States Patent
Chobotov

(10) Patent No.: US 8,801,769 B2
(45) Date of Patent: *Aug. 12, 2014

(54) ENDOVASCULAR GRAFT

(71) Applicant: TriVascular, Inc., Santa Rosa, CA (US)

(72) Inventor: Michael V. Chobotov, Santa Rosa, CA (US)

(73) Assignee: TriVascular, Inc., Santa Rosa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/737,351

(22) Filed: Jan. 9, 2013

(65) Prior Publication Data

US 2013/0131786 A1 May 23, 2013

Related U.S. Application Data

(63) Continuation of application No. 12/566,793, filed on Sep. 25, 2009, now Pat. No. 8,361,136, which is a continuation of application No. 11/390,732, filed on Mar. 28, 2006, now Pat. No. 7,615,071, which is a continuation of application No. 10/132,754, filed on Apr. 24, 2002, now Pat. No. 7,081,129, which is a continuation of application No. 09/133,978, filed on Aug. 14, 1998, now Pat. No. 6,395,019.

(60) Provisional application No. 60/074,112, filed on Feb. 9, 1998.

(51) Int. Cl.
*A61M 29/00* (2006.01)
*A61F 11/00* (2006.01)

(52) U.S. Cl.
USPC ....... 623/1.13; 623/1.23; 623/1.25; 623/1.36; 623/1.37; 606/108; 606/191; 606/194; 606/198

(58) Field of Classification Search
USPC ................. 623/1.13, 1.36, 1.37, 1.23, 1.25; 606/108, 191, 194, 195, 198
See application file for complete search history.

(56) References Cited

U.S. PATENT DOCUMENTS

| 3,540,431 A | 11/1970 | Uddin |
| 3,631,854 A | 1/1972 | Fryer |

(Continued)

FOREIGN PATENT DOCUMENTS

| EP | 0407566 | 1/1990 |
| EP | 0480667 | 4/1992 |

(Continued)

OTHER PUBLICATIONS

Haimovitch, L. and Patterson, N., "Robust growth is forecast for endovascular repair fo AAAs," *The BBI Newsletter*, vol. 26, No. 5, pp. 113-144, (May 2003).

(Continued)

*Primary Examiner* — Vy Q. Bui
(74) *Attorney, Agent, or Firm* — Hoffmann & Baron, LLP

(57) ABSTRACT

An endovascular graft, which is configured to conform to the morphology of a vessel to be treated, includes a tubular ePTFE structure; an inflatable ePTFE structure disposed over at least a portion of the ePTFE tubular structure; and an injection port in fluid communication with the inflatable ePTFE structure for inflation of the inflatable ePTFE structure with an inflation medium. The inflatable ePTFE structure may be longitudinally disposed over the tubular ePTFE structure. The ePTFE structure may be a bifurcated structure having first and second bifurcated tubular structures, where the inflatable ePTFE structure is disposed over at least a portion of the first and second bifurcated tubular structures.

15 Claims, 9 Drawing Sheets

(56) References Cited

U.S. PATENT DOCUMENTS

| | | |
|---|---|---|
| 3,657,744 A | 4/1972 | Ersek |
| 3,814,137 A | 6/1974 | Martinez |
| 3,818,511 A | 6/1974 | Goldberg et al. |
| 3,900,027 A | 8/1975 | Keedwell |
| 3,902,198 A | 9/1975 | Cooper |
| 3,991,767 A | 11/1976 | Miller, Jr. et al. |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,434,797 A | 3/1984 | Silander |
| 4,459,252 A | 7/1984 | MacGregor |
| 4,474,630 A | 10/1984 | Planck et al. |
| 4,497,074 A | 2/1985 | Rey et al. |
| 4,512,338 A | 4/1985 | Balko et al. |
| 4,550,447 A | 11/1985 | Seiler, Jr. et al. |
| 4,552,707 A | 11/1985 | How |
| 4,562,596 A | 1/1986 | Kornberg |
| 4,577,631 A | 3/1986 | Kreamer |
| 4,580,568 A | 4/1986 | Gianturco |
| 4,592,754 A | 6/1986 | Gupte et al. |
| 4,617,932 A | 10/1986 | Kornberg |
| 4,647,416 A | 3/1987 | Seiler, Jr. et al. |
| 4,655,769 A | 4/1987 | Zachariades |
| 4,655,771 A | 4/1987 | Wallsten |
| 4,665,906 A | 5/1987 | Jervis |
| 4,705,517 A | 11/1987 | DiPisa, Jr. |
| 4,731,073 A | 3/1988 | Robinson |
| 4,739,762 A | 4/1988 | Palmaz |
| 4,740,207 A | 4/1988 | Kreamer |
| 4,776,337 A | 10/1988 | Palmaz |
| 4,787,899 A | 11/1988 | Lazarus |
| 4,816,028 A | 3/1989 | Kapadia et al. |
| 4,830,003 A | 5/1989 | Wolff et al. |
| 4,856,516 A | 8/1989 | Hillstead |
| 4,941,870 A | 7/1990 | Okada et al. |
| 4,955,899 A | 9/1990 | Della Corna et al. |
| 4,957,669 A | 9/1990 | Primm |
| 5,019,090 A | 5/1991 | Pinchuk |
| 5,064,435 A | 11/1991 | Porter |
| 5,100,422 A | 3/1992 | Berguer et al. |
| 5,104,399 A | 4/1992 | Lazarus |
| 5,104,400 A | 4/1992 | Berguer et al. |
| 5,108,424 A | 4/1992 | Hoffman, Jr. et al. |
| 5,116,365 A | 5/1992 | Hillstead |
| 5,122,154 A | 6/1992 | Rhodes |
| 5,123,917 A | 6/1992 | Lee |
| 5,139,480 A | 8/1992 | Hickle et al. |
| 5,151,105 A | 9/1992 | Kwan-Gett |
| 5,152,782 A | 10/1992 | Kowligi et al. |
| 5,156,620 A | 10/1992 | Pigott |
| 5,171,252 A | 12/1992 | Friedland |
| 5,171,262 A | 12/1992 | MacGregor |
| 5,195,984 A | 3/1993 | Schatz |
| 5,197,976 A | 3/1993 | Herweck et al. |
| 5,207,695 A | 5/1993 | Trout, III |
| 5,219,355 A | 6/1993 | Parodi et al. |
| 5,226,913 A | 7/1993 | Pinchuk |
| 5,234,447 A | 8/1993 | Kaster et al. |
| 5,275,622 A | 1/1994 | Lazarus et al. |
| 5,282,847 A | 2/1994 | Trescony et al. |
| 5,290,305 A | 3/1994 | Inoue |
| 5,316,023 A | 5/1994 | Palmaz et al. |
| 5,330,528 A | 7/1994 | Lazim |
| 5,334,201 A | 8/1994 | Cowan |
| 5,344,426 A | 9/1994 | Lau et al. |
| 5,344,444 A | 9/1994 | Glastra |
| 5,354,310 A | 10/1994 | Garnic et al. |
| 5,354,329 A | 10/1994 | Whalen |
| 5,360,443 A | 11/1994 | Barone et al. |
| 5,366,504 A | 11/1994 | Andersen et al. |
| 5,370,682 A | 12/1994 | Schmitt |
| 5,370,691 A | 12/1994 | Samson |
| 5,383,892 A | 1/1995 | Cardon et al. |
| 5,387,235 A | 2/1995 | Chuter |
| 5,397,345 A | 3/1995 | Lazarus et al. |
| 5,397,355 A | 3/1995 | Marin et al. |
| 5,405,377 A | 4/1995 | Cragg |
| 5,405,379 A | 4/1995 | Lane |
| 5,411,550 A | 5/1995 | Herweck et al. |
| 5,423,851 A | 6/1995 | Samuels |
| 5,443,498 A | 8/1995 | Fontaine |
| 5,447,152 A | 9/1995 | Kohsai et al. |
| 5,456,713 A | 10/1995 | Chuter |
| 5,464,419 A | 11/1995 | Glastra |
| 5,464,449 A | 11/1995 | Ryan et al. |
| 5,476,506 A | 12/1995 | Lunn |
| 5,480,423 A | 1/1996 | Ravenscroft et al. |
| 5,489,295 A | 2/1996 | Piplani et al. |
| 5,507,769 A | 4/1996 | Marin et al. |
| 5,507,770 A | 4/1996 | Turk |
| 5,522,880 A | 6/1996 | Barone et al. |
| 5,522,881 A | 6/1996 | Lentz |
| 5,527,353 A | 6/1996 | Schmitt |
| 5,527,355 A | 6/1996 | Ahn |
| 5,529,653 A | 6/1996 | Glastra |
| 5,534,024 A | 7/1996 | Rogers et al. |
| 5,536,274 A | 7/1996 | Neuss |
| 5,554,180 A | 9/1996 | Turk |
| 5,556,426 A | 9/1996 | Popadiuk et al. |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,571,079 A | 11/1996 | Bello et al. |
| 5,571,171 A | 11/1996 | Barone et al. |
| 5,571,173 A | 11/1996 | Parodi |
| 5,575,817 A | 11/1996 | Martin |
| 5,578,071 A | 11/1996 | Parodi |
| 5,578,072 A | 11/1996 | Barone et al. |
| 5,591,229 A | 1/1997 | Parodi |
| 5,597,378 A | 1/1997 | Jervis |
| 5,607,468 A | 3/1997 | Rogers et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,624,685 A | 4/1997 | Takahashi et al. |
| 5,628,782 A | 5/1997 | Myers et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,653,746 A | 8/1997 | Schmitt |
| 5,662,675 A | 9/1997 | Polanskyj Stockert |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,452 A | 11/1997 | Barone et al. |
| 5,683,453 A | 11/1997 | Palmaz |
| 5,693,084 A | 12/1997 | Chuter |
| 5,693,087 A | 12/1997 | Parodi |
| 5,693,088 A * | 12/1997 | Lazarus ................ 623/1.35 |
| 5,697,968 A | 12/1997 | Rogers et al. |
| 5,700,285 A | 12/1997 | Myers et al. |
| 5,707,378 A | 1/1998 | Ahn et al. |
| 5,707,388 A | 1/1998 | Lauterjung |
| 5,709,701 A | 1/1998 | Parodi |
| 5,709,703 A | 1/1998 | Lukic et al. |
| 5,713,917 A | 2/1998 | Leonhardt et al. |
| 5,716,395 A | 2/1998 | Myers et al. |

(56) References Cited

U.S. PATENT DOCUMENTS

| | | |
|---|---|---|
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,733,325 A | 3/1998 | Robinson et al. |
| 5,735,892 A | 4/1998 | Myers et al. |
| 5,735,897 A | 4/1998 | Buirge |
| 5,741,325 A | 4/1998 | Chaikof et al. |
| 5,747,128 A | 5/1998 | Campbell et al. |
| 5,749,880 A | 5/1998 | Banas et al. |
| 5,749,920 A | 5/1998 | Quiachon et al. |
| 5,755,772 A | 5/1998 | Evans et al. |
| 5,769,882 A | 6/1998 | Fogarty et al. |
| 5,769,885 A | 6/1998 | Quiachon et al. |
| 5,769,887 A | 6/1998 | Brown et al. |
| 5,780,807 A | 7/1998 | Saunders |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,799,384 A | 9/1998 | Schwartz et al. |
| 5,800,512 A | 9/1998 | Lentz et al. |
| 5,800,518 A | 9/1998 | Piplani et al. |
| 5,800,524 A | 9/1998 | Borghi |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,827,320 A | 10/1998 | Richter et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,843,170 A | 12/1998 | Ahn |
| 5,855,598 A | 1/1999 | Pinchuk |
| 5,858,556 A | 1/1999 | Eckert et al. |
| 5,871,536 A | 2/1999 | Lazarus |
| 5,871,537 A | 2/1999 | Holman et al. |
| 5,871,538 A | 2/1999 | Dereume |
| 5,873,906 A | 2/1999 | Lau et al. |
| 5,876,432 A | 3/1999 | Lau et al. |
| 5,906,641 A | 5/1999 | Thompson et al. |
| 5,916,264 A | 6/1999 | Von Oepen et al. |
| 5,925,061 A | 7/1999 | Ogi et al. |
| 5,925,075 A | 7/1999 | Myers et al. |
| 5,926,650 A | 7/1999 | Suzuki et al. |
| 5,931,865 A | 8/1999 | Silverman et al. |
| 5,944,750 A | 8/1999 | Tanner et al. |
| 5,957,973 A | 9/1999 | Quiachon et al. |
| 5,961,545 A | 10/1999 | Lentz et al. |
| 5,961,546 A | 10/1999 | Robinson et al. |
| 5,968,090 A | 10/1999 | Ratcliff et al. |
| 5,972,441 A | 10/1999 | Campbell et al. |
| 5,976,179 A | 11/1999 | Inoue |
| 5,976,192 A | 11/1999 | McIntyre et al. |
| 5,976,650 A | 11/1999 | Campbell et al. |
| 5,984,956 A | 11/1999 | Tweden et al. |
| 5,989,287 A | 11/1999 | Yang et al. |
| 5,993,481 A | 11/1999 | Marcade et al. |
| 5,993,489 A | 11/1999 | Lewis et al. |
| 5,997,573 A | 12/1999 | Quijano et al. |
| 6,001,123 A | 12/1999 | Lau |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,017,362 A | 1/2000 | Lau |
| 6,017,364 A | 1/2000 | Lazarus |
| 6,019,787 A | 2/2000 | Richard et al. |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,702 A | 3/2000 | Bachinski et al. |
| 6,036,723 A | 3/2000 | Anidjar et al. |
| 6,039,755 A | 3/2000 | Edwin et al. |
| 6,039,758 A | 3/2000 | Quichon et al. |
| 6,042,605 A | 3/2000 | Martin et al. |
| 6,042,606 A | 3/2000 | Frantzen |
| 6,045,557 A | 4/2000 | White et al. |
| 6,051,020 A | 4/2000 | Coicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,063,114 A | 5/2000 | Nash et al. |
| 6,077,296 A | 6/2000 | Shokoohi et al. |
| 6,077,297 A | 6/2000 | Robinson et al. |
| 6,090,128 A | 7/2000 | Douglas |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,110,198 A | 8/2000 | Fogarty et al. |
| 6,117,168 A | 9/2000 | Yang et al. |
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,143,015 A | 11/2000 | Nobles |
| 6,143,022 A | 11/2000 | Shull et al. |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,956 A | 11/2000 | Pierce |
| 6,153,292 A | 11/2000 | Bell et al. |
| 6,156,063 A | 12/2000 | Douglas |
| 6,159,237 A | 12/2000 | Alt et al. |
| 6,159,239 A | 12/2000 | Greenhalgh |
| 6,159,565 A | 12/2000 | Campbell et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,620 B1 | 1/2001 | Kerr |
| 6,183,504 B1 | 2/2001 | Inoue |
| 6,187,036 B1 | 2/2001 | Shaolian et al. |
| 6,193,745 B1 | 2/2001 | Fogarty et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,568 B1 | 3/2001 | Lombardi et al. |
| 6,210,422 B1 | 4/2001 | Douglas |
| 6,210,434 B1 | 4/2001 | Quichon et al. |
| 6,210,435 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,235,050 B1 | 5/2001 | Quiachon et al. |
| 6,238,432 B1 | 5/2001 | Parodi |
| 6,241,759 B1 | 6/2001 | Piplani et al. |
| 6,245,097 B1 | 6/2001 | Inoue |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,133 B1 | 6/2001 | Richter et al. |

(56) References Cited

U.S. PATENT DOCUMENTS

| | | |
|---|---|---|
| 6,254,632 B1 | 7/2001 | Wu et al. |
| 6,261,317 B1 | 7/2001 | Inoue |
| 6,264,684 B1 | 7/2001 | Banas et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,330 B1 | 9/2001 | Johansson et al. |
| 6,287,335 B1 | 9/2001 | Drasler et al. |
| 6,293,968 B1 | 9/2001 | Taheri |
| 6,293,969 B1 | 9/2001 | Chuter |
| 6,296,661 B1 | 10/2001 | Davila et al. |
| 6,302,891 B1 | 10/2001 | Nadal |
| 6,302,906 B1 | 10/2001 | Goicoechea et al. |
| 6,302,908 B1 | 10/2001 | Parodi |
| 6,306,164 B1 | 10/2001 | Kujawski |
| 6,312,458 B1 | 11/2001 | Golds |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,328,762 B1 | 12/2001 | Anderson et al. |
| 6,331,188 B1 | 12/2001 | Lau et al. |
| 6,331,190 B1 | 12/2001 | Shokochi et al. |
| 6,331,191 B1 | 12/2001 | Chobotov |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,346,118 B1 | 2/2002 | Baker et al. |
| 6,352,553 B1 | 3/2002 | van der Burg et al. |
| 6,352,561 B1 | 3/2002 | Leopold et al. |
| 6,355,055 B1 | 3/2002 | Waksman et al. |
| 6,355,056 B1 | 3/2002 | Pinheiro |
| 6,355,063 B1 | 3/2002 | Calcote |
| 6,357,104 B1 | 3/2002 | Myers |
| 6,361,637 B2 | 3/2002 | Martin et al. |
| 6,364,904 B1 | 4/2002 | Smith |
| 6,368,355 B1 | 4/2002 | Uflacker |
| 6,379,382 B1 | 4/2002 | Yang |
| 6,383,213 B2 | 5/2002 | Wilson et al. |
| 6,387,124 B1 | 5/2002 | Buscemi et al. |
| 6,395,019 B2 | 5/2002 | Chobotov |
| 6,395,022 B1 | 5/2002 | Piplani et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,756 B1 | 6/2002 | Murphy |
| 6,409,757 B1 | 6/2002 | Trout et al. |
| 6,416,535 B1 | 7/2002 | Lazarus |
| 6,416,537 B1 | 7/2002 | Martakos et al. |
| 6,416,542 B1 | 7/2002 | Marcade et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,571 B1 | 8/2002 | Lentz et al. |
| 6,432,131 B1 | 8/2002 | Ravenscroft |
| 6,432,132 B1 | 8/2002 | Cottone et al. |
| 6,436,133 B1 | 8/2002 | Furst et al. |
| 6,436,135 B1 | 8/2002 | Goldfarb |
| 6,440,165 B1 | 8/2002 | Richter et al. |
| 6,443,981 B1 | 9/2002 | Colone et al. |
| 6,451,047 B2 | 9/2002 | McCrea et al. |
| 6,451,050 B1 | 9/2002 | Rudakov et al. |
| 6,451,053 B1 | 9/2002 | Dehdashtian et al. |
| 6,454,795 B1 | 9/2002 | Chuter |
| 6,454,796 B1 | 9/2002 | Barkman et al. |
| 6,464,721 B1 | 10/2002 | Marcade et al. |
| 6,464,722 B2 | 10/2002 | Israel et al. |
| 6,471,721 B1 | 10/2002 | Dang |
| 6,475,236 B1 | 11/2002 | Roubin et al. |
| 6,475,238 B1 | 11/2002 | Fedida |
| 6,482,166 B1 | 11/2002 | Fariabi |
| 6,482,227 B1 | 11/2002 | Solovay |
| 6,485,513 B1 | 11/2002 | Fan |
| 6,488,701 B1 | 12/2002 | Nolting et al. |
| 6,488,705 B2 | 12/2002 | Schmitt et al. |
| 6,491,719 B1 | 12/2002 | Fogary et al. |
| 6,494,904 B1 | 12/2002 | Love |
| 6,494,909 B2 | 12/2002 | Greenhaigh |
| 6,497,722 B1 | 12/2002 | Von Oepen et al. |
| 6,497,868 B1 | 12/2002 | Tanahashi |
| 6,500,203 B1 | 12/2002 | Thompson et al. |
| 6,500,204 B1 | 12/2002 | Igaki |
| 6,506,211 B1 | 1/2003 | Skubitz et al. |
| 6,508,833 B2 | 1/2003 | Pavcnik et al. |
| 6,517,571 B1 | 2/2003 | Brauker et al. |
| 6,517,574 B1 | 2/2003 | Chuter |
| 6,520,984 B1 | 2/2003 | Garrison et al. |
| 6,521,284 B1 | 2/2003 | Parsons et al. |
| 6,524,334 B1 | 2/2003 | Thompson |
| 6,533,811 B1 | 3/2003 | Ryan et al. |
| 6,537,202 B1 | 3/2003 | Frantzen |
| 6,540,778 B1 | 4/2003 | Quiachon et al. |
| 6,547,814 B2 | 4/2003 | Edwin et al. |
| 6,547,815 B2 | 4/2003 | Myers |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,582,458 B1 | 6/2003 | White et al. |
| 6,599,275 B1 | 7/2003 | Fischer, Jr. |
| 6,613,082 B2 | 9/2003 | Yang |
| 6,613,083 B2 | 9/2003 | Alt |
| 6,613,084 B2 | 9/2003 | Yang |
| 6,652,570 B2 | 11/2003 | Smith et al. |
| 6,673,103 B1 | 1/2004 | Golds et al. |
| 6,685,736 B1 | 2/2004 | White et al. |
| 6,689,158 B1 | 2/2004 | White et al. |
| 6,689,159 B2 | 2/2004 | Lau et al. |
| 6,692,523 B2 | 2/2004 | Holman et al. |
| 6,695,875 B2 | 2/2004 | Stelter et al. |
| 6,706,064 B1 | 3/2004 | Anson |
| 6,709,455 B1 | 3/2004 | Chouinard |
| 6,719,783 B2 | 4/2004 | Lentz et al. |
| 6,740,115 B2 | 5/2004 | Lombardi |
| 2001/0002443 A1 | 5/2001 | Parodi |
| 2001/0004705 A1 | 6/2001 | Killion et al. |
| 2001/0007955 A1 | 7/2001 | Drasler et al. |
| 2001/0010013 A1 | 7/2001 | Cox et al. |
| 2001/0011188 A1 | 8/2001 | Berry et al. |
| 2001/0014823 A1 | 8/2001 | Ressemann et al. |
| 2001/0016770 A1 | 8/2001 | Allen et al. |
| 2001/0018610 A1 | 8/2001 | Limon |
| 2001/0020184 A1 | 9/2001 | Dehdashtian et al. |
| 2001/0023370 A1 | 9/2001 | Smith et al. |
| 2001/0027338 A1 | 10/2001 | Greenberg |
| 2001/0027339 A1 | 10/2001 | Boatman et al. |
| 2001/0029349 A1 | 10/2001 | Leschinsky |
| 2001/0029397 A1 | 10/2001 | Thompson |
| 2001/0037142 A1 | 11/2001 | Stelter et al. |
| 2001/0037146 A1 | 11/2001 | Lau et al. |
| 2001/0037147 A1 | 11/2001 | Lau et al. |
| 2001/0039446 A1 | 11/2001 | Edwin et al. |
| 2001/0041928 A1 | 11/2001 | Pavcnik et al. |
| 2001/0044652 A1 | 11/2001 | Moore |
| 2001/0047198 A1 | 11/2001 | Drasler et al. |
| 2001/0049534 A1 | 12/2001 | Lachat |
| 2001/0049550 A1 | 12/2001 | Martin et al. |
| 2001/0053929 A1 | 12/2001 | Vonesh et al. |
| 2002/0002397 A1 | 1/2002 | Martin et al. |
| 2002/0007193 A1 | 1/2002 | Tanner et al. |
| 2002/0007212 A1 | 1/2002 | Brown et al. |
| 2002/0016623 A1 | 2/2002 | Kula et al. |
| 2002/0016626 A1 | 2/2002 | DiMatteo et al. |
| 2002/0016627 A1 | 2/2002 | Golds |
| 2002/0019665 A1 | 2/2002 | Dehdashtian et al. |
| 2002/0026231 A1 | 2/2002 | Shannon et al. |
| 2002/0026235 A1 | 2/2002 | Anderson et al. |

(56) References Cited

U.S. PATENT DOCUMENTS

| | | |
|---|---|---|
| 2002/0032408 A1 | 3/2002 | Parker et al. |
| 2002/0040235 A1 | 4/2002 | Holman et al. |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0042645 A1 | 4/2002 | Shannon |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052645 A1 | 5/2002 | Kugler et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0082675 A1 | 6/2002 | Myers |
| 2002/0091440 A1 | 7/2002 | Calcote |
| 2002/0096252 A1 | 7/2002 | Lukic |
| 2002/0098278 A1 | 7/2002 | Bates et al. |
| 2002/0099434 A1 | 7/2002 | Buscemi et al. |
| 2002/0099436 A1 | 7/2002 | Thornton et al. |
| 2002/0107561 A1 | 8/2002 | Pinheiro |
| 2002/0111633 A1 | 8/2002 | Stoltze et al. |
| 2002/0111665 A1 | 8/2002 | Lauterjung |
| 2002/0111669 A1 | 8/2002 | Pazienza et al. |
| 2002/0116047 A1 | 8/2002 | Vardi et al. |
| 2002/0116048 A1 | 8/2002 | Chobotov |
| 2002/0116051 A1 | 8/2002 | Cragg |
| 2002/0120321 A1 | 8/2002 | Gunderson et al. |
| 2002/0120325 A1 | 8/2002 | Richter et al. |
| 2002/0120327 A1 | 8/2002 | Cox et al. |
| 2002/0123790 A1 | 9/2002 | White et al. |
| 2002/0128703 A1 | 9/2002 | Ravenscroft |
| 2002/0128706 A1 | 9/2002 | Osypka |
| 2002/0133221 A1 | 9/2002 | Schatz |
| 2002/0138048 A1 | 9/2002 | Tuch |
| 2002/0138126 A1 | 9/2002 | Camrud et al. |
| 2002/0138129 A1 | 9/2002 | Armstrong et al. |
| 2002/0143381 A1 | 10/2002 | Gilligan et al. |
| 2002/0147492 A1 | 10/2002 | Shokoohi et al. |
| 2002/0151954 A1 | 10/2002 | Brenneman |
| 2002/0156518 A1 | 10/2002 | Tehrani |
| 2002/0156521 A1 | 10/2002 | Ryan et al. |
| 2002/0156522 A1 | 10/2002 | Ivancev et al. |
| 2002/0165602 A1 | 11/2002 | Douglas et al. |
| 2002/0165603 A1 | 11/2002 | Thornton et al. |
| 2002/0165607 A1 | 11/2002 | Alt |
| 2002/0169499 A1 | 11/2002 | Zilla et al. |
| 2002/0173836 A1 | 11/2002 | Pinchuk |
| 2002/0173837 A1 | 11/2002 | Lauterjung |
| 2002/0183825 A1 | 12/2002 | Solem |
| 2002/0193871 A1 | 12/2002 | Beyersdorf et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2002/0198588 A1 | 12/2002 | Armstrong et al. |
| 2003/0004559 A1 | 1/2003 | Lentz et al. |
| 2003/0006528 A1 | 1/2003 | Edwin et al. |
| 2003/0009211 A1 | 1/2003 | DiCarlo |
| 2003/0009212 A1 | 1/2003 | Kerr |
| 2003/0060871 A1 | 3/2003 | Hill et al. |
| 2003/0074048 A1 | 4/2003 | Sherry |
| 2003/0074050 A1 | 4/2003 | Kerr |
| 2003/0074058 A1 | 4/2003 | Sherry |
| 2003/0093145 A1 | 5/2003 | Lawrence-Brown et al. |
| 2003/0097170 A1 | 5/2003 | Friedrich et al. |
| 2003/0097174 A1 | 5/2003 | Henderson |
| 2003/0125797 A1 | 7/2003 | Chobotov et al. |
| 2003/0143330 A1 | 7/2003 | Loomis et al. |
| 2003/0216802 A1 | 11/2003 | Chobotov |
| 2004/0024446 A1 | 2/2004 | Smith |
| 2004/0049264 A1 | 3/2004 | Sowinski et al. |
| 2004/0054397 A1 | 3/2004 | Smith et al. |
| 2004/0073190 A1 | 4/2004 | Deem et al. |
| 2004/0073287 A1 | 4/2004 | Goicoechea et al. |
| 2004/0082989 A1 | 4/2004 | Cook et al. |
| 2004/0093068 A1 | 5/2004 | Bergen et al. |
| 2004/0098115 A1 | 5/2004 | Goicoechea et al. |
| 2004/0106978 A1 | 6/2004 | Greenberg et al. |

FOREIGN PATENT DOCUMENTS

| | | |
|---|---|---|
| EP | 0646151 | 6/1992 |
| EP | 0502905 | 9/1992 |
| EP | 0541443 | 5/1993 |
| EP | 0617930 | 5/1994 |
| EP | 0646365 | 4/1995 |
| EP | 0664107 | 7/1995 |
| EP | 0473694 | 12/1995 |
| EP | 0473727 | 12/1995 |
| EP | 0689806 | 1/1996 |
| EP | 0712614 | 5/1996 |
| EP | 0714641 | 6/1996 |
| EP | 0747069 | 12/1996 |
| EP | 0775472 | 5/1997 |
| EP | 0792627 | 9/1997 |
| EP | 0808613 | 11/1997 |
| EP | 0809997 | 12/1997 |
| EP | 0821979 | 2/1998 |
| EP | 0734235 | 2/1999 |
| EP | 0814729 | 8/2000 |
| EP | 1029518 | 8/2000 |
| EP | 0441516 | 3/2001 |
| EP | 1093772 | 4/2001 |
| EP | 1121945 | 8/2001 |
| EP | 0821648 | 9/2001 |
| EP | 0808140 | 12/2001 |
| EP | 1163889 | 12/2001 |
| EP | 1208817 | 5/2002 |
| EP | 1212987 | 6/2002 |
| EP | 1212988 | 6/2002 |
| EP | 1212989 | 6/2002 |
| EP | 1212991 | 6/2002 |
| EP | 0877582 | 10/2002 |
| EP | 1148843 | 4/2003 |
| EP | 0997115 | 10/2003 |
| EP | 1380270 | 1/2004 |
| EP | 1051135 | 3/2004 |
| EP | 1405613 | 4/2004 |
| EP | 1415617 | 4/2004 |
| EP | 1426020 | 6/2004 |
| JP | 5161665 | 6/1993 |
| WO | WO 90/08801 | 8/1990 |
| WO | WO 90/14055 | 11/1990 |
| WO | WO 91/00792 | 6/1991 |
| WO | WO 92/00043 | 1/1992 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/03754 | 2/1995 |
| WO | WO 95/09585 | 4/1995 |
| WO | WO 95/09586 | 4/1995 |
| WO | WO 95/11720 | 5/1995 |
| WO | WO 95/16406 | 6/1995 |
| WO | WO 96/10967 | 4/1996 |
| WO | WO 96/24308 | 8/1996 |
| WO | WO 96/28115 | 9/1996 |
| WO | WO 97/03624 | 2/1997 |
| WO | WO 97/07751 | 3/1997 |
| WO | WO 97/25938 | 7/1997 |
| WO | WO 97/27820 | 8/1997 |
| WO | WO 97/27959 | 8/1997 |
| WO | WO 97/29716 | 8/1997 |
| WO | WO 97/33533 | 9/1997 |
| WO | WO 97/37616 | 10/1997 |
| WO | WO 97/41804 | 11/1997 |
| WO | WO 98/06355 | 2/1998 |
| WO | WO 98/10806 | 3/1998 |

(56) References Cited

FOREIGN PATENT DOCUMENTS

| | | |
|---|---|---|
| WO | WO 98/12989 | 4/1998 |
| WO | WO 98/27894 | 7/1998 |
| WO | WO 98/30156 | 7/1998 |
| WO | WO 98/33453 | 8/1998 |
| WO | WO 98/36708 | 8/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 98/55047 | 12/1998 |
| WO | WO 99/00073 | 1/1999 |
| WO | WO 99/11199 | 3/1999 |
| WO | WO 99/32051 | 7/1999 |
| WO | WO 99/38455 | 8/1999 |
| WO | WO 99/39662 | 8/1999 |
| WO | WO 99/39663 | 8/1999 |
| WO | WO 99/43378 | 9/1999 |
| WO | WO 99/43379 | 9/1999 |
| WO | WO 99/47078 | 9/1999 |
| WO | WO 99/65419 | 12/1999 |
| WO | WO 00/10487 | 3/2000 |
| WO | WO 00/19943 | 5/2000 |
| WO | WO 00/33769 | 6/2000 |
| WO | WO 00/42947 | 7/2000 |
| WO | WO 00/42948 | 7/2000 |
| WO | WO 00/45741 | 8/2000 |
| WO | WO 00/51522 | 9/2000 |
| WO | WO 00/53251 | 9/2000 |
| WO | WO 01/01886 | 1/2001 |
| WO | WO 01/01887 | 1/2001 |
| WO | WO 01/15633 | 3/2001 |
| WO | WO 01/21102 | 3/2001 |
| WO | WO 01/21107 | 3/2001 |
| WO | WO 01/21108 | 3/2001 |
| WO | WO 01/28456 | 4/2001 |
| WO | WO 01/30270 | 5/2001 |
| WO | WO 01/39700 | 6/2001 |
| WO | WO 01/41675 | 6/2001 |
| WO | WO 01/52771 | 7/2001 |
| WO | WO 01/52914 | 7/2001 |
| WO | WO 01/66037 | 9/2001 |
| WO | WO 01/66038 | 9/2001 |
| WO | WO 01/67993 | 9/2001 |
| WO | WO 01/74270 | 10/2001 |
| WO | WO 02/36332 | 5/2002 |
| WO | WO 02/087651 | 11/2002 |
| WO | WO 02/100454 | 12/2002 |
| WO | WO 03/000308 | 1/2003 |
| WO | WO 03/003946 | 1/2003 |
| WO | WO 03/008005 | 1/2003 |
| WO | WO 03/015837 | 2/2003 |
| WO | WO 03/026713 | 4/2003 |
| WO | WO 03/084440 | 10/2003 |
| WO | WO 03/094795 | 11/2003 |
| WO | WO 03/094797 | 11/2003 |
| WO | WO 03/094799 | 11/2003 |
| WO | WO 2004/002370 | 1/2004 |
| WO | WO 2004/004603 | 1/2004 |
| WO | WO 2004/004966 | 1/2004 |
| WO | WO 2004/016193 | 2/2004 |
| WO | WO 2004/017866 | 3/2004 |
| WO | WO 2004/017867 | 3/2004 |
| WO | WO 2004/021931 | 3/2004 |
| WO | WO 2004/037116 | 5/2004 |
| WO | WO 2004/045393 | 6/2004 |

OTHER PUBLICATIONS

Blum, et al., "Endoluminal stent-grafts for infrarenal abdominal aortic aneurysms," *N Engl J. Med*, 336(1):13-20, (1997).
Ernst, "Current therapy for infrarenal aortic aneurysms," *N Engl J Med*, 336(1):59-60, (1997).
Moore, et al., "Transfemoral endovascular repair of abdominal aortic aneurysm; results of the North American EVT phase 1 trail,"*J Vasc Surg*, 23(4):543-553, (1996).
Parodi, "Endovascular repair of abdominal aortic aneurysms and other arterial lesions," *J Vasc Surg*, 21(4):549-557, (1995).
Parodi, et al., "Transfemoral intraluminal graft implantation for abdominal aortic aneurysms," *Ann Vasc Surg*, 5(6):491-499, (1991).
Uflacker, et al., "Endovascular treatment of abdominal aortic aneurysms: a review," *Eur. Radiol.*, 11:739-19753 (2001).
European Search Report for EP 09013660.7, dated Dec. 29, 2009.
US 6,413,270, 07/2002, Thornton et al. (withdrawn)

\* cited by examiner

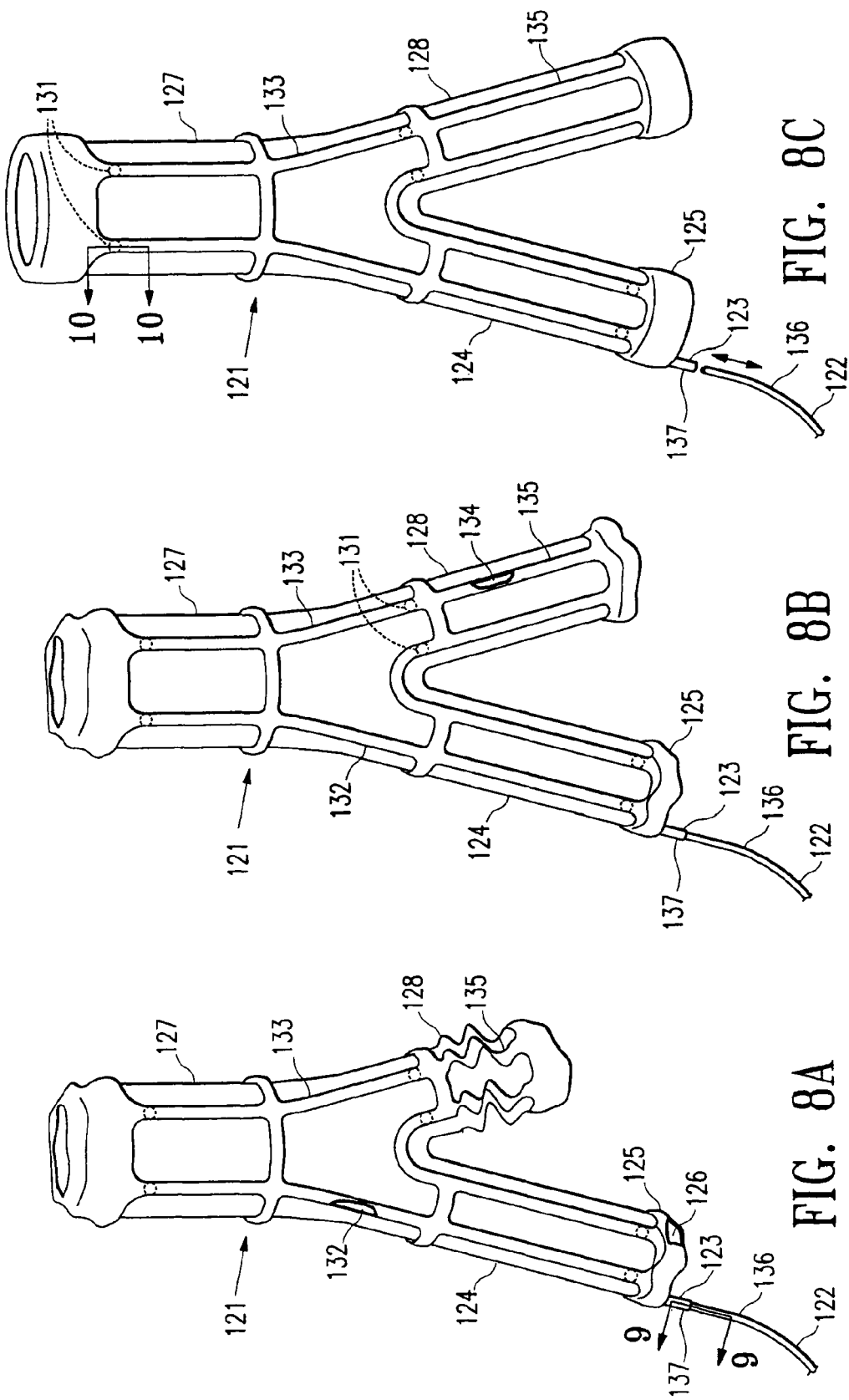

ENDOVASCULAR GRAFT

CROSS-REFERENCE TO RELATED APPLICATIONS

This application is a continuation of U.S. application Ser. No. 12/566,793, filed Sep. 25, 2009, now U.S. Pat. No. 8,361,136; which is a continuation of U.S. application Ser. No. 11/390,732, filed Mar. 28, 2006, now U.S. Pat. No. 7,615,071; which is a continuation of U.S. application Ser. No. 10/132,754, filed Apr. 24, 2002, now U.S. Pat. No. 7,081,129; which is a continuation of U.S. application Ser. No. 09/133,978, filed Aug. 14, 1998, now U.S. Pat. No. 6,395,019; which claims the benefit of U.S. Provisional Application No. 60/074,112, filed Feb. 9, 1998, the contents of all of which are incorporated herein by reference.

BACKGROUND OF THE INVENTION

The present invention relates to a system and method for the treatment of disorders of the vasculature. More specifically, a system and method for treatment of abdominal aortic aneurysm and the like, which is a condition manifested by expansion and weakening of the aorta below the diaphragm. Such conditions require intervention due to the severity of the sequelae, which frequently is death. Prior methods of treating aortic aneurysm have consisted of invasive surgical methods with graft placement within the aorta as a reinforcing member of the artery. However, such a procedure requires a surgical cut down to access the vessel, which in turn can result in a catastrophic rupture of the aneurysm due to the decreased external pressure from the organs and tissues surrounding the aorta, which are moved during the procedure to gain access to the vessel. Accordingly, surgical procedures have a high mortality rate due to the possibility of the rupture discussed above in addition to other factors. Other factors can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W.B. Saunders Company.

Due to the inherent risks and complexities of surgical procedures, various attempts have been made in the development of alternative methods for deployment of grafts within aortic aneurysms. One such method is the non-invasive technique of percutaneous delivery by a catheter-based system. Such a method is described in Lawrence, Jr. et al. in "Percutaneous endovascular graft: experimental evaluation", *Radiology* (May 1987). Lawrence described therein the use of a Giant-urco stent as disclosed in U.S. Pat. No. 4,580,568. The stent is used to position a Dacron fabric graft within the vessel. The Dacron graft is compressed within the catheter and then deployed within the vessel to be treated. A similar procedure has also been described by Mirich et al. in "Percutaneously placed endovascular grafts for aortic aneurysms: feasibility study," *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery catheters used to deliver the grafts are relatively large in profile, often up to 24 French and greater, and stiff in bending. The large profile and bending stiffness makes delivery through the irregular and tortuous arteries of diseased vessels difficult and risky. In particular, the iliac arteries are often too narrow or irregular for the passage of a percutaneous device. Because of this, non-invasive percutaneous graft delivery for treatment of aortic aneurysm is not available to many patients who would benefit from it.

Another contraindication for current percutaneous grafting methods and devices is a vessel treatment site with high neck angulation which precludes a proper fit between the graft and the vessel wall. An improper fit or seal between the graft and the vessel wall can result in leaks or areas of high stress imposed upon the diseased vessel which lead to reduced graft efficacy and possibly rupture of the aneurysm.

While the above methods have shown some promise with regard to treating abdominal aortic aneurysms with non-invasive methods, there remains a need for an endovascular graft system which can be deployed percutaneously in a small diameter flexible catheter system. In addition, there is a need for a graft which conforms more closely to the contours of an aortic aneurysm which are often quite irregular and angulated and vary from patient to patient. The present invention satisfies these and other needs.

SUMMARY OF THE INVENTION

The present invention is directed generally to an endovascular graft for vascular treatment and a method for manufacturing and using the graft. The graft generally has an inflatable tubular frame structure which can be configured to conform to the morphology of a patient's vessel to be treated. The frame structure has a proximal end and a distal end with an inflatable cuff disposed on at least one end and preferably both. The inflatable cuffs can be reduced in diameter and profile when deflated for introduction into a patient's vasculature by a catheter based delivery system or other suitable means. The inflatable cuffs provide a sufficiently rigid structure when inflated which supports the graft and seals the graft against the interior surface of the vessel in which it is being deployed. One or more elongated inflatable channels may also be disposed on the graft. Preferably, the elongated channel is disposed between and in fluid communication with a proximal and distal inflatable cuff. The channel provides the desired stiffness upon inflation, prevents kinking of the graft frame, and facilitates deployment of the graft within a patient's body passageway. The elongated inflatable channel can be in a longitudinal or linear configuration with respect to the graft, but is preferably shaped as a helix disposed about the graft. Other orientations such as interconnecting grids or rings may also be suitable for the elongated channels. The inflatable cuffs and the elongated channel contain fluid tight chambers which are generally in fluid communication with each other but which may also be separated by valves or rupture discs therein to selectively control the sequence of inflation or deployment. The fluid tight chambers are typically accessed by an injection port which is configured to accept a pressurized source of gas, fluid, particles, gel or combination thereof and which is in fluid particle, gel or combination thereof and which is a fluid communication with at least one of the fluid tight chambers. A fluid which sets, hardens or gels over time can also be used. The number of elongated channels can vary with the specific configuration of the graft as adapted to a given indication, but generally, the number of channels ranges from 1 to 25, preferably 2 to about 8.

A proximal neck portion may be secured to the proximal inflatable cuff. The proximal neck portion has a flexible tubular structure that has a diameter similar to the proximal inflatable cuff. The proximal neck portion can be configured as a straight tubular section or can be tapered distally or proximally to an increased or decreased diameter. Preferably, the proximal neck portion is secured and sealed to the proximal inflatable cuff and tapers proximally to an increased diameter so as to engage the inside surface of a vessel wall which provides a sealing function in addition to that of the proximal inflatable cuff. Such a configuration also smoothes the transition for fluid flow from the vessel of a patient to the lumen or channel within the endovascular graft. The proximal neck portion has an inlet axis that preferably has an angular bias with respect to a longitudinal axis of the graft.

Preferably, the graft has a monolithic structure wherein the material that comprises the inflatable cuffs and channels extends between these elements in a thin flexible layer that defines a longitudinal lumen to confine a flow of blood or other fluid therethrough. Such a monolithic structure can be made from a variety of suitable polymers including PVC, polyurethane, polyethylene and fluoropolymers such as TFE, PTFE and ePTFE. Additional stiffness or reinforcement can be added to the graft by the addition of metal or plastic inserts or battens to the graft, which can also facilitate positioning and deployment of the graft prior to inflation of an inflatable portion of the graft.

In another embodiment, the graft has a thin flexible layer disposed over or between a proximal inflatable cuff, a distal inflatable cuff, and an elongated inflatable channel of the frame. The thin flexible layer is made of a material differing from the material of the cuffs or elongated channel. The barrier is shaped so as to form a tubular structure defining a longitudinal lumen or channel to confine a flow of blood therethrough. The flexible barrier may be made of a variety of suitable materials such as DACRON®, NYLON®, or fluoropolymers such as TEFLON® or the like.

An endovascular graft having features of the invention may be made in a tubular configuration of a flexible layer material such as Dacron, Nylon or fluoropolymers as discussed above. The inflatable cuffs and elongated channels are formed separately and bonded thereto. The inflatable cuffs and channels may also be made from the same layer material, i.e., Dacron, Teflon, or Nylon with a fluid impermeable membrane or bladder disposed within the cuff or channel so as to make it fluid tight. To limit permeability, the material in the regions of the cuffs and channels may also be treated with a coating or otherwise be processed by methods such as thermo-mechanical compaction.

In one embodiment of the invention, an expansion member is attached to the proximal end of the frame structure of the graft or to a proximal neck portion of the graft. Expansion members may also be attached to the distal end of the graft. Preferably, the expansion member is made of an expandable ring or linked expandable rings of pseudoelastic shape memory alloy which is self expanding and helps to mechanically anchor the proximal end of the graft to a body channel to prevent axial displacement of the graft once it is deployed. By having an expansion member which is distinct from the proximal cuff, the sealing function of the cuff, which requires supple conformation to the vessel wall without excessive radial force, can be separated from the anchoring function of the expansion member, which can require significant radial force. This allows each function to be optimized without compromising the function of the other. It also allows the anchoring function which can require more radial force on the vessel wall to be located more proximal from the aneurysm than the cuff, and therefor be positioned in a healthier portion of the vessel which is better able to withstand the radial force required for the anchoring function. In addition, the cuff and expansion members can be separated spatially in a longitudinal direction with the graft in a collapsed state for delivery which allows for a lower more flexible profile for percutaneous delivery. Such a configuration makes a collapsed delivery profile of 12-16 French possible, preferably below 12 French.

The expandable ring or rings of the expansion member may be formed in a continuous loop having a serpentine or zig-zag pattern along a circumference of the loop. Any other similar configuration could be used that would allow radial expansion of the ring. The expansion member may be made of suitable high strength metals such as stainless steel, Nitinol or other shape memory alloys, or other suitable high strength composites or polymers. The expansion member may be made from high memory materials such as Nitinol or low memory materials such as stainless steel depending on the configuration of the endovascular graft, the morphology of the deployment site, and the mode of delivery and deployment of the graft.

The expansion member preferably has an inlet axis which forms an inlet axis angle in relation to a longitudinal axis of the graft. The angled inlet axis allows the graft to better conform to the morphology of a patient's vasculature in patients who have an angulated neck aneurysm morphology. The inlet axis angle can be from about 0 to about 90 degrees, preferably about 20 degrees to about 30 degrees. Some or all of the inlet axis angle can be achieved in a proximal neck portion of the graft, to which the expansion member may be attached. An expansion member or members may also be attached to the distal end of the graft.

In another embodiment of the invention, the graft may be bifurcated at the distal end of a main body portion of the graft and have at least two bifurcated portions with longitudinal lumens in fluid communication with a longitudinal lumen of the main body portion. The first bifurcated portion and second bifurcated portion can be formed from a structure similar to that of a main body portion with optional inflatable cuffs at either the proximal or distal end. One or more elongated channels can be disposed between the inflatable cuffs.

The size and angular orientation of the bifurcated portions can vary, however, they are generally configured to have an outer diameter that is compatible with the inner diameter of a patient's iliac arteries. The bifurcated portions can also be adapted to use in a patient's renal arteries or other suitable indication. The distal ends of the bifurcated portions may also have expansion members attached thereto in order to anchor or expand, or both anchor and expand said distal ends within the body passageway being treated. The expansion members for the distal ends of the bifurcated portions can have similar structure to the expansion member attached to the proximal end or proximal neck portion of the main body portion. The expansion members are preferably made from a shape memory material such as Nitinol.

In bifurcated embodiments of grafts having features of the invention which also have a biased proximal end which forms an inlet axis angle, the direction of the bias or angulation can be important with regard to achieving a proper fit between the graft and the morphology of the deployment site. Generally, the angular bias of the proximal end of the graft, proximal neck portion or proximal expansion member can be in any direction. Preferably, the angular bias is in a direction normal to a plane defined by a longitudinal axis of the main body portion, the first bifurcated portion and the second bifurcated portion.

In another embodiment of the invention, rupture discs or other temporary closures are placed between fluid tight chambers of the inflatable cuffs and elongated channel or channels of the graft and form a seal between the chambers. The rupture discs may be burst or broken if sufficient force or pressure is exerted on one side of a disc or temporary closure. Once the graft is located at the site to be treated within a body passageway of a patient, a pressurized gas, fluid or gel may be injected by an inflation catheter into one of the fluid tight chambers of the graft through an injection port. Injection of a pressurized substance into an inflatable cuff will cause the cuff to take a generally annular shape, although the cuff can conform to the shape of the vessel within which it is deployed, and exert a sufficient radial force outward against the inner surface of the body passageway to be treated in order to provide the desired sealing function.

Multiple rupture discs can be disposed in various locations of the graft and also be configured to rupture at different pressures or burst thresholds to facilitate deployment of the graft within a body passageway. In a particular bifurcated embodiment of the invention, the proximal inflatable cuff of the main body portion may be positioned proximal of a junction between the branch of the abdominal aorta and the iliac arteries of a patient. As the proximal cuff is deployed by injection of an appropriate substance into an injection port in fluid communication with the fluid tight chamber thereof, it will expand radially and become axially and sealingly fixed proximal to the bifurcation of the aorta. A rupture disc is located between the fluid tight chamber of the proximal cuff and the elongated inflatable channels so that the proximal cuff may be substantially deployed before the rupture disc bursts and the elongated channels begin to fill with the injected substance. The elongated channels then fill and become sufficiently rigid and expand to create a longitudinal lumen therein. As pressure is increased within the fluid tight chamber, a rupture disc between the fluid tight chamber of the elongated channels and a fluid tight chamber of the optional distal inflatable cuff or distal manifold of the main body portion will burst and the distal inflatable cuff or manifold will deploy and become pressurized. One of the bifurcated portions of the graft may then be deployed as a rupture disc sealing its fluid tight chamber from the distal inflatable cuff or manifold of the main body portion of the graft bursts as the inflation pressure is increased. Finally, the second bifurcated portion of the graft deploys after a rupture disc sealing its fluid tight chamber from the main body portion bursts.

An inflation catheter which is attached to and in fluid communication with the fluid tight chambers of the graft via an injection port disposed thereon can be decoupled from the injection port after completion of inflation by elevating pressure above a predetermined level. The elevated pressure causes a break in a connection with the injection port by triggering a disconnect mechanism. Alternatively, the inflation catheter can be unscrewed from its connection. The injection port can include a check valve, seal or plug to close off the egress of inflation material once the inflation catheter has been decoupled. The injection port could also be glued or twisted to seal it off.

A graft having features of the invention may also be deployed by percutaneous delivery with a catheter based system which has an inflatable balloon member disposed within expansion members of the graft in a collapsed state. The graft is percutaneously delivered to a desired site. Once the graft is axially positioned, the inflatable member of the balloon may be expanded and the expansion members forced radially against the interior surface of a body channel within which it is disposed. The expansion members may also be self expanding from a constrained configuration once the constraint is removed. After the graft has been positioned by the catheter system, the inflatable cuff or cuffs and elongated channel or channels of the graft are pressurized.

These and other advantages of the invention will become more apparent from the following detailed description of the invention when taken in conjunction with the accompanying exemplary drawings.

BRIEF DESCRIPTION OF THE DRAWINGS

FIGS. 8A, 8B and 8C depict perspective views of a bifurcated endovascular graft having features of the present invention in various stages of deployment.

DETAILED DESCRIPTION OF THE INVENTION

Figure 1:
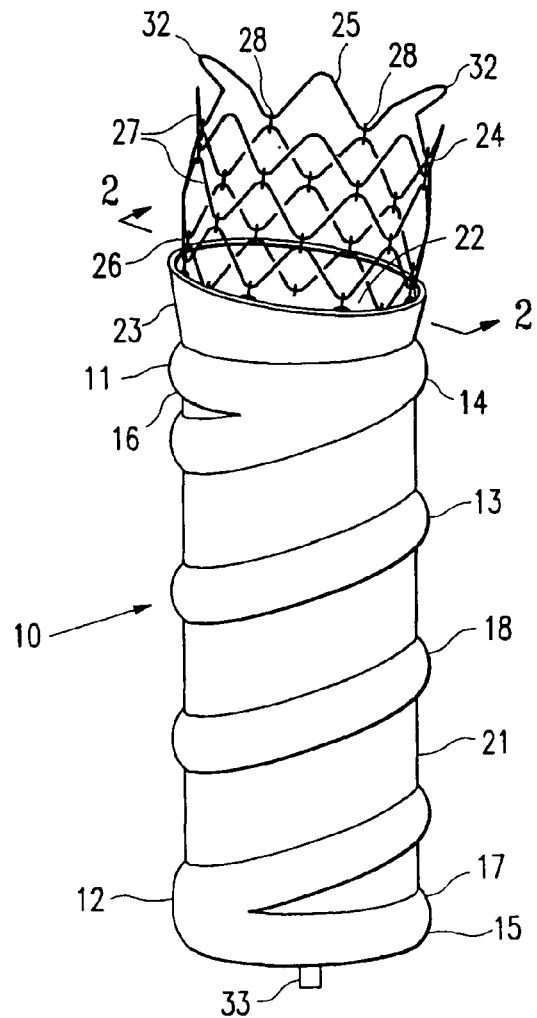
FIG. 1 shows a perspective view of an endovascular graft having features of the invention.

FIG. 1 shows a perspective view of an endovascular graft 10 having features of the present invention and having a proximal end 11 and a distal end 12. The graft is supported by an inflatable frame 13 which has a proximal end 14 and a distal end 15 and is shown in its deployed state. The inflatable frame structure 13 has a proximal inflatable cuff 16 at the proximal end 14 and an optional distal inflatable cuff 17 at the distal end 15. The inflatable cuffs 16 and 17 can be annular in shape when deployed, although the cuffs can confirm to the shape of the vessel within which they are deployed, and can have an outside diameter or cross sectional dimension of about 10 to about 45 mm, preferably about 16 to about 28 mm. There is at least one elongated inflatable channel 18 disposed between the proximal inflatable cuff 16 and the distal inflatable cuff 17. The inflatable frame 13 can be from about 5 to about 30 cm in length, preferably about 10 to about 20 cm in length. Disposed between the proximal inflatable cuff 16, the distal inflatable cuff 17 and the elongated inflatable channel 18 is a thin flexible layer 21 that forms a longitudinal lumen 22 which can confine a flow of fluid therethrough. The thin flexible layer 21 may be made from the same material as the inflatable cuffs 16 and 17 and elongated channel 18 and be integral with the construction of those elements forming a monolithic structure. The thin flexible layer 21 and the materials used to form the frame structure 13 can have a wall thickness of about 0.1 to about 0.5 mm, preferably about 0.15 to about 0.25 mm. The inflatable frame 13 may be constructed from any suitable medical polymer or other material, including fluoropolymers, PVCs, polyurethanes, PET, ePTFE and the like. Preferably the inflatable frame 13 and thin flexible layer 21 are made from ePTFE. A proximal heck portion 23 is attached to the proximal end of the inflatable frame structure 13 and serves as an additional means to seal the graft against the inside of a body passageway, provides a means of biasing a proximal end of the graft 11, and provides a smooth flow transition into longitudinal lumen 22.

An expansion member 24 having a proximal end 25 and a distal end 26 has the distal end secured to the proximal end 14 of the frame 13. The distal end 26 of the expansion member may also be secured to the proximal neck portion 23. The expansion member 24 can be made from expandable rings 27 formed in a zig-zag pattern and connected by links 28. The expansion member 24 is preferably a self-expanding member that expands to contact the inside wall of a body passage upon release from a constrained state. The expansion member 24 may be made from any suitable material that permits expansion from a constrained state, preferably a shape memory alloy such as Nitinol. The expansion member 24 may be configured to self expand from a constrained state or be configured to expand as a result of an outward radial force applied from within. Other materials suitable for construction of the expansion member 24 include stainless steel, MP35N alloy, shape memory alloys other than Nitinol, fiber composites and the like. The links 28 allow articulation of the expansion member 24 to traverse curvature of a patient's anatomy both during delivery and in situ. The expansion member 24 has a generally cylindrical shape but may also have outwardly directed protuberances 32 that are designed to engage the inside surface of a body passage. The expansion member 24 is generally cylindrical in shape when deployed, although the expansion member can conform to the shape of the vessel within which it is deployed, and can have a length of about 0.5 to about 5 cm, preferably about 1 to about 4 cm. The diameter of the expansion member 24 is typically similar to that of the inflatable cuffs 16 and 17, and can be about 10 to about 35 mm, preferably about 16 to about 28 mm. The high strength material from which the expansion member 24 is made can have a cross sectional dimension of about 0.1 to about 1.5 mm, preferably about 0.25 to about 1 mm.

The graft 10 is generally deployed by inflation of the inflatable frame structure 13 with a pressurized material of solid particles, gas, fluid or gel which can be injected through an injection port 33. The pressurized material may contain a contrast medium which facilitates imaging of the device while being deployed within a patient's body. For example, radiopaque materials such as bismuth, barium, gold, platinum, tantalum or the like may be used in particulate or powder form to facilitate visualization of the graft under fluoroscopy. Fixed radiopaque markers may also be attached or integrally molded into the graft for the same purpose, and may be made from the same radiopaque materials discussed above.

Figure 2:
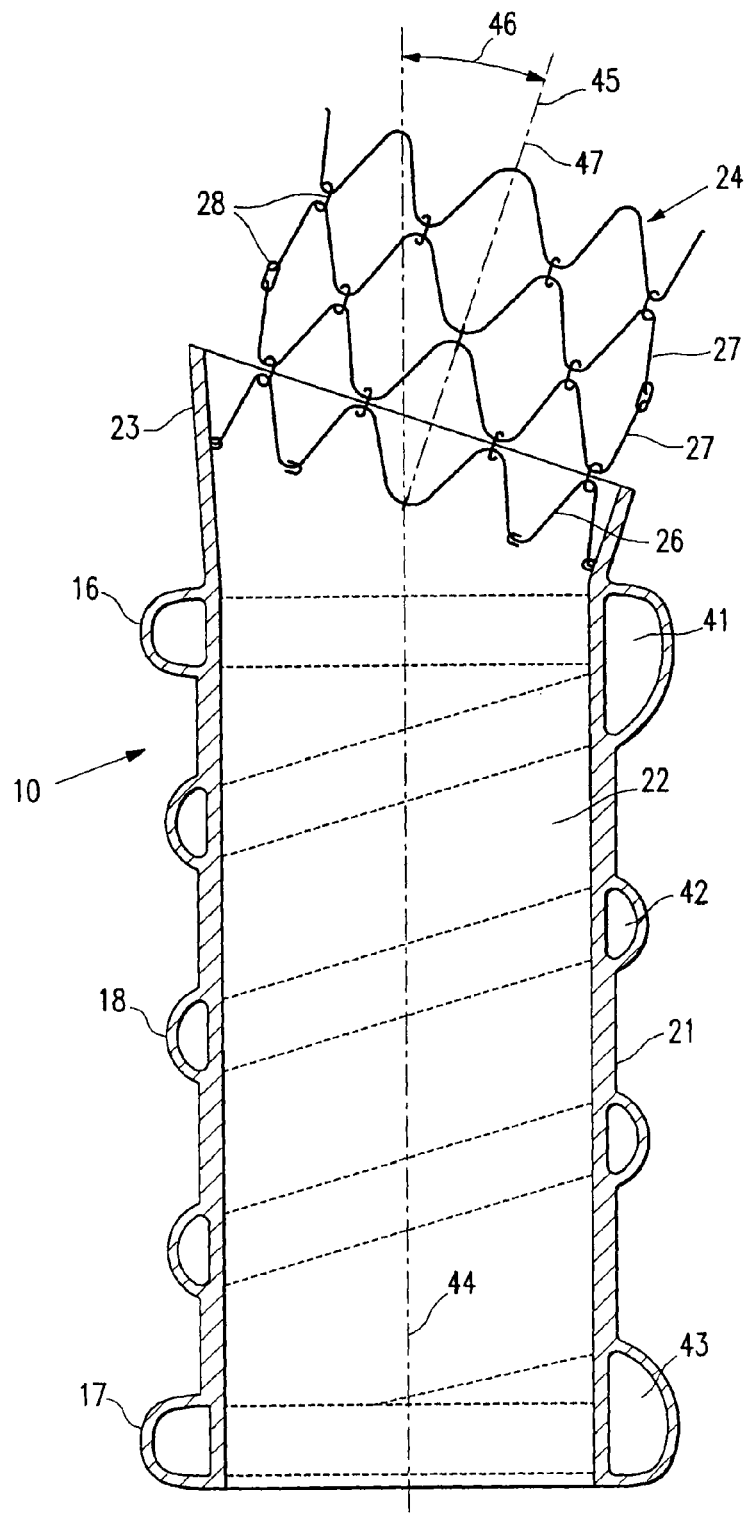
FIG. 2 shows a longitudinal cross sectional view of an endovascular graft having a monolithic structure.

FIG. 2 shows a longitudinal cross sectional view of the endovascular graft shown in FIG. 1. Within the proximal inflatable cuff 16 is a fluid tight chamber 41 which is in fluid communication with a fluid tight chamber 42 of the elongated inflatable channel 18. The fluid tight chamber 42 of the elongated inflatable channel is in fluid communication with a fluid tight chamber 43 within the optional distal inflatable cuff 17. A longitudinal axis 44 of the graft 10 is shown in addition to a proximal inlet axis 45 which forms an inlet axis angle 46 with the longitudinal axis. The angled inlet axis 45 is generally created by the proximal neck portion 23 and provides the graft with a profile which can conform to the morphology of a patient's vasculature. The expansion member 24 has a longitudinal axis 47 which is generally coextensive with the proximal inlet axis 45, but can further bend to conform to local anatomy including neck angulation of a diseased vessel.

Figure 3:
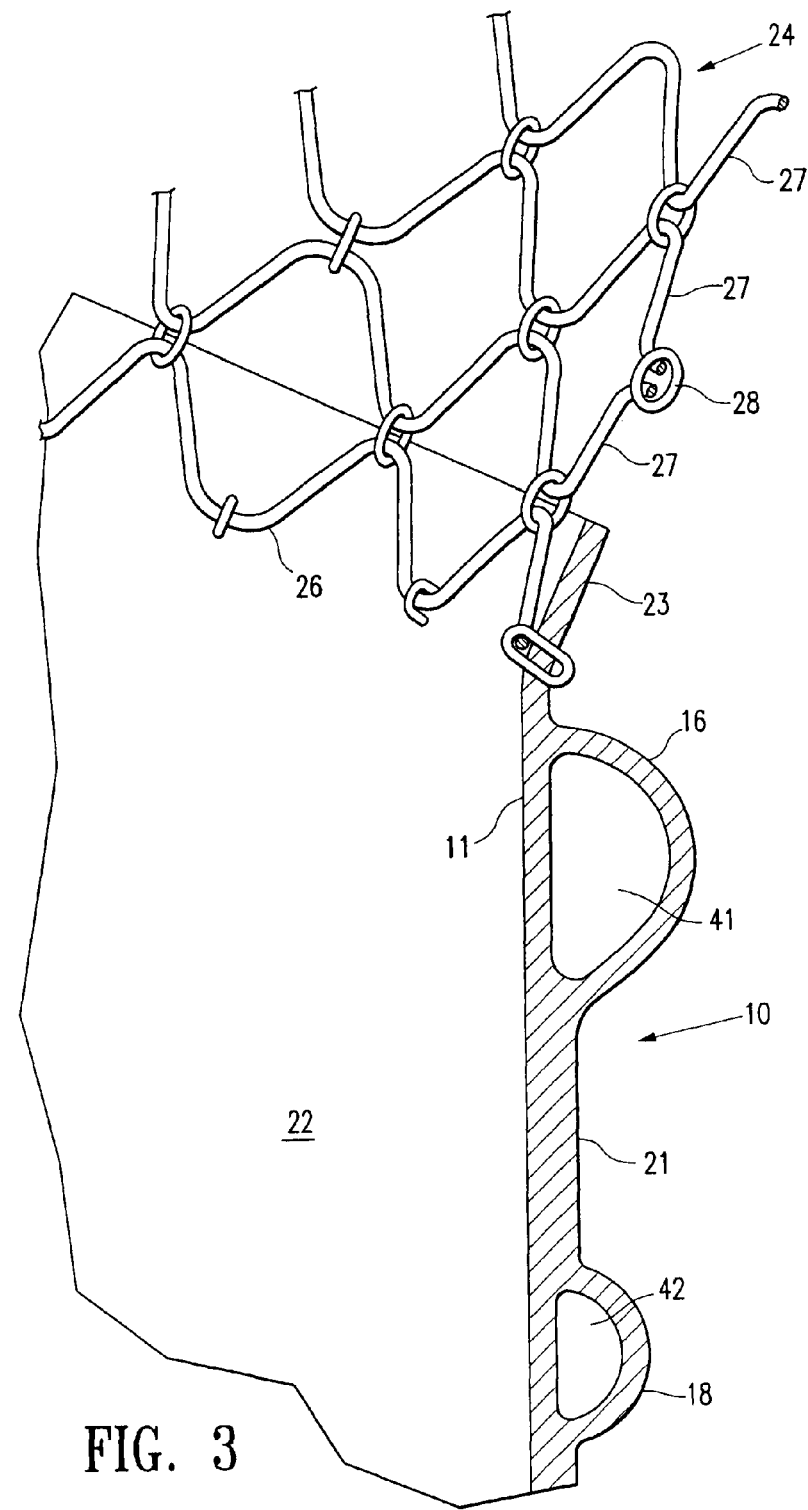
FIG. 3 shows an enlarged view of the longitudinal cross sectional view of the endovascular graft of FIG. 2.

FIG. 3 shows an enlarged view of the longitudinal cross sectional view of a portion of the proximal end 11 of the graft 10 shown in FIG. 2. A more detailed view of the fluid tight chamber 41 of the proximal inflatable cuff 16 can be seen as well as a more detailed view of the attachment of the distal end 26 of the expansion member 24 to the proximal neck portion 23. The thin flexible layer 21 can be seen disposed between the proximal inflatable cuff 16 and the elongated inflatable channel 18. The expandable rings 27 of the expansion member 24 are connected by links 28 which can be made from the same material as the expansion member or any other suitable material such as a biocompatible fiber or a metal such as stainless steel or Nitinol.

Figure 4:
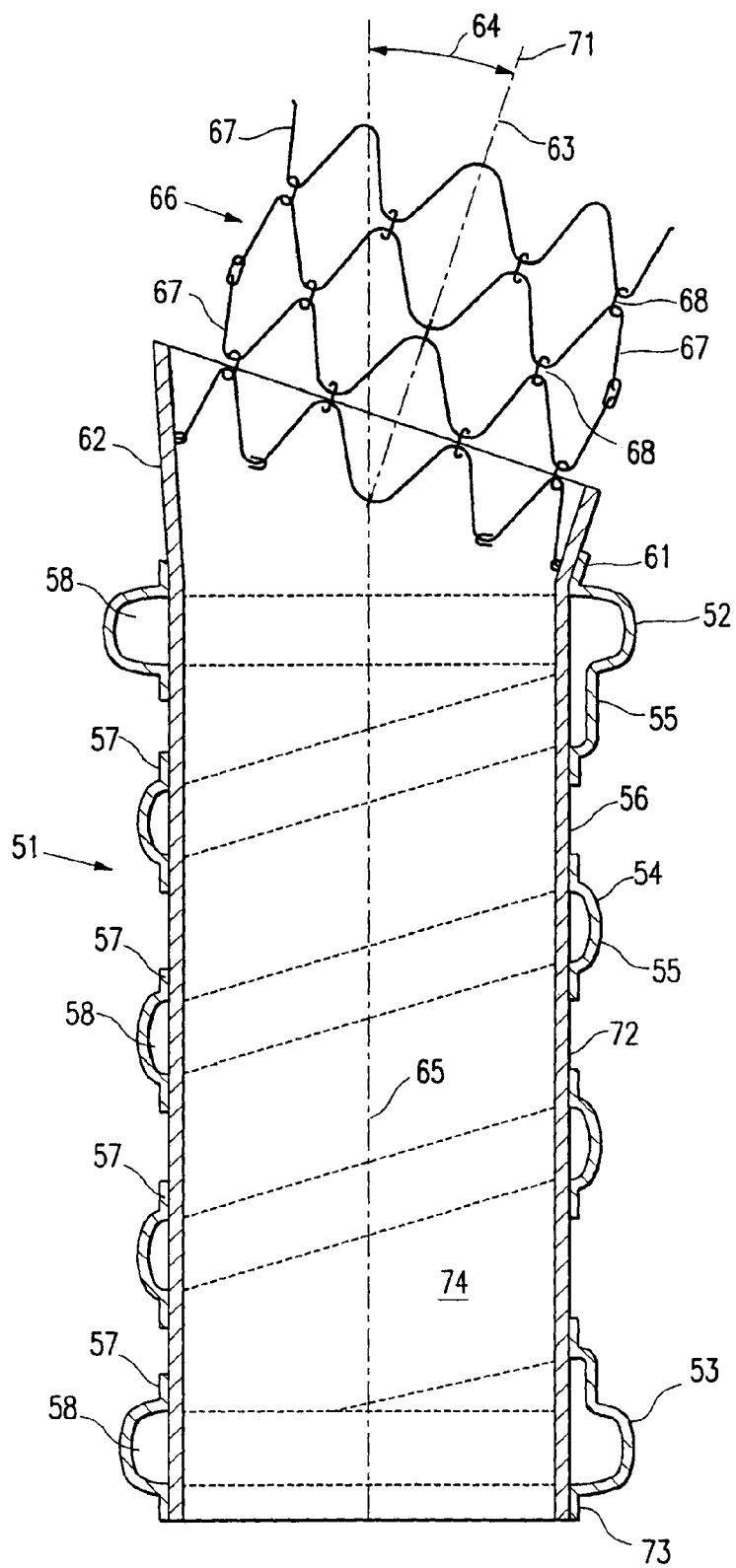
FIG. 4 shows a longitudinal cross-sectional view of an endovascular graft having features of the invention.

FIG. 4 is a transverse cross-sectional view of an embodiment of an endovascular graft 51, having features of the invention. The proximal inflatable cuff 52, distal inflatable cuff 53, and elongated inflatable channel 54 are formed by sealingly bonding strips of material 55 over a tubular structure 56. The strips 55 are bonded at the edges 57 so as to form fluid tight chambers 58 therein. If the material of the strips 55 which have been bonded to the tubular structure 56 are of a permeable character, an additional material may be used to coat the inside of the fluid tight chambers in order to make them impermeable to fluids. Alternatively, the material of the strips 55 and the material of the elongated tubular member 56 adjacent thereto may be made impermeable by undergoing further thermal, mechanical, or chemical processing. Preferably, thermo-mechanical compaction would be used to render the fluid tight chambers 58 impermeable to fluids which would be suitable for inflating the graft 51.

The proximal end 61 of the graft 51 has a proximal neck portion 62 which has an inlet axis 63 which forms an inlet axis angle 64 with a longitudinal axis 65 of the graft. The inlet axis angle 64 allows the graft 51 to better conform to morphology of a patient's vascular channels. An expansion member 66 is also located at the proximal end 61 of the graft 51 and is formed of expandable rings 67 held together by links 68. The expansion member 66 has a longitudinal axis 71 which can coincide with the inlet axis 63 of the proximal neck portion 62. The graft 51 has a thin flexible layer 72 which extends from the distal end 73 of the graft 51, to the proximal end of the graft 61, including the proximal neck portion 62. The thin flexible layer 72 forms a longitudinal lumen or channel 74 upon deployment of the graft, which confines a flow of blood or other bodily fluid therethrough.

Figure 5:
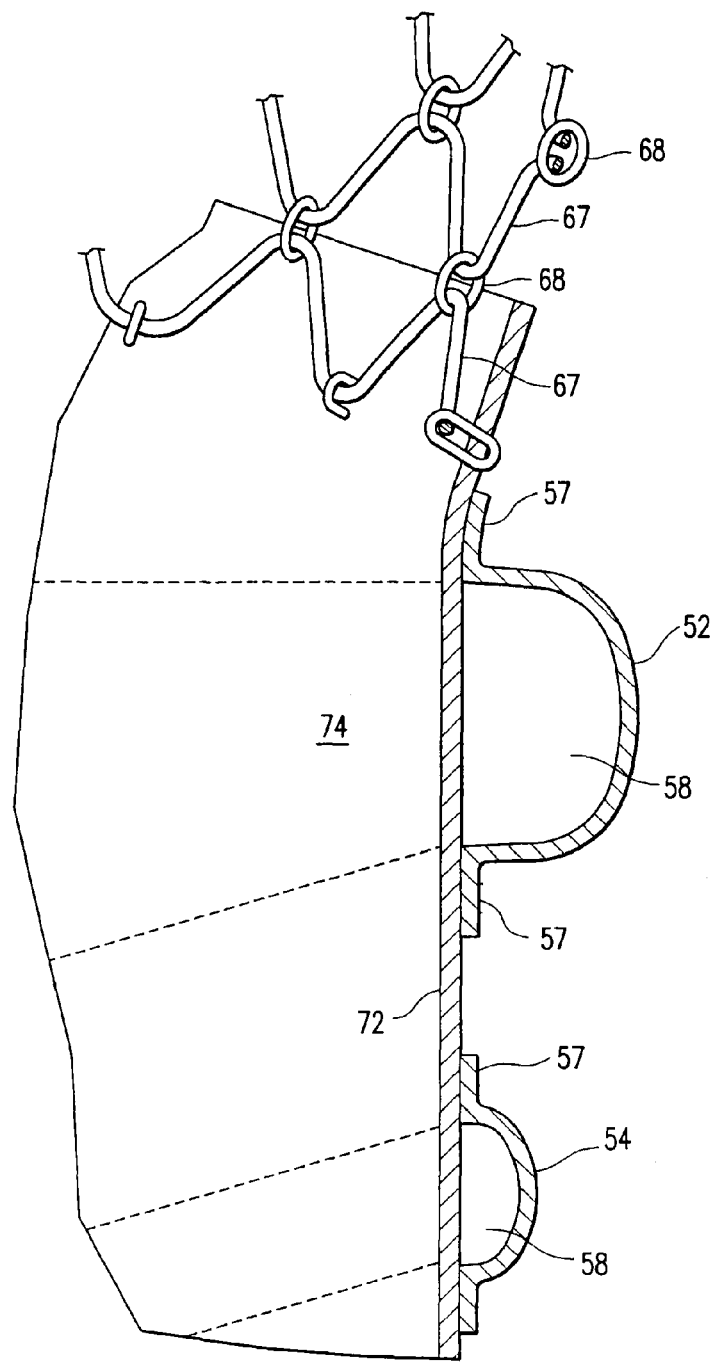
FIG. 5 shows an enlarged view of a portion of the endovascular graft shown in FIG. 4.

FIG. 5 is an enlarged view of the longitudinal cross-sectional view of the endovascular graft of FIG. 4. A more detailed view of the fluid tight chamber 58 of the proximal inflatable cuff and elongated inflatable channel can be seen. The edges of the strips 57 which form the proximal inflatable cuff 52 and the elongated inflatable channel 54 are bonded at the edges by any suitable technique such as the use of adhesives, solvents, or heat. Suitable adhesives would include epoxies and cyanoacrylates or the like. Materials suitable for use as the thin flexible layer 72 or the strips 55 includes Dacron, Nylon, Teflon, and also such materials as PVC, polyethylene, polyurethane and ePTFE.

Figures 6, 7:
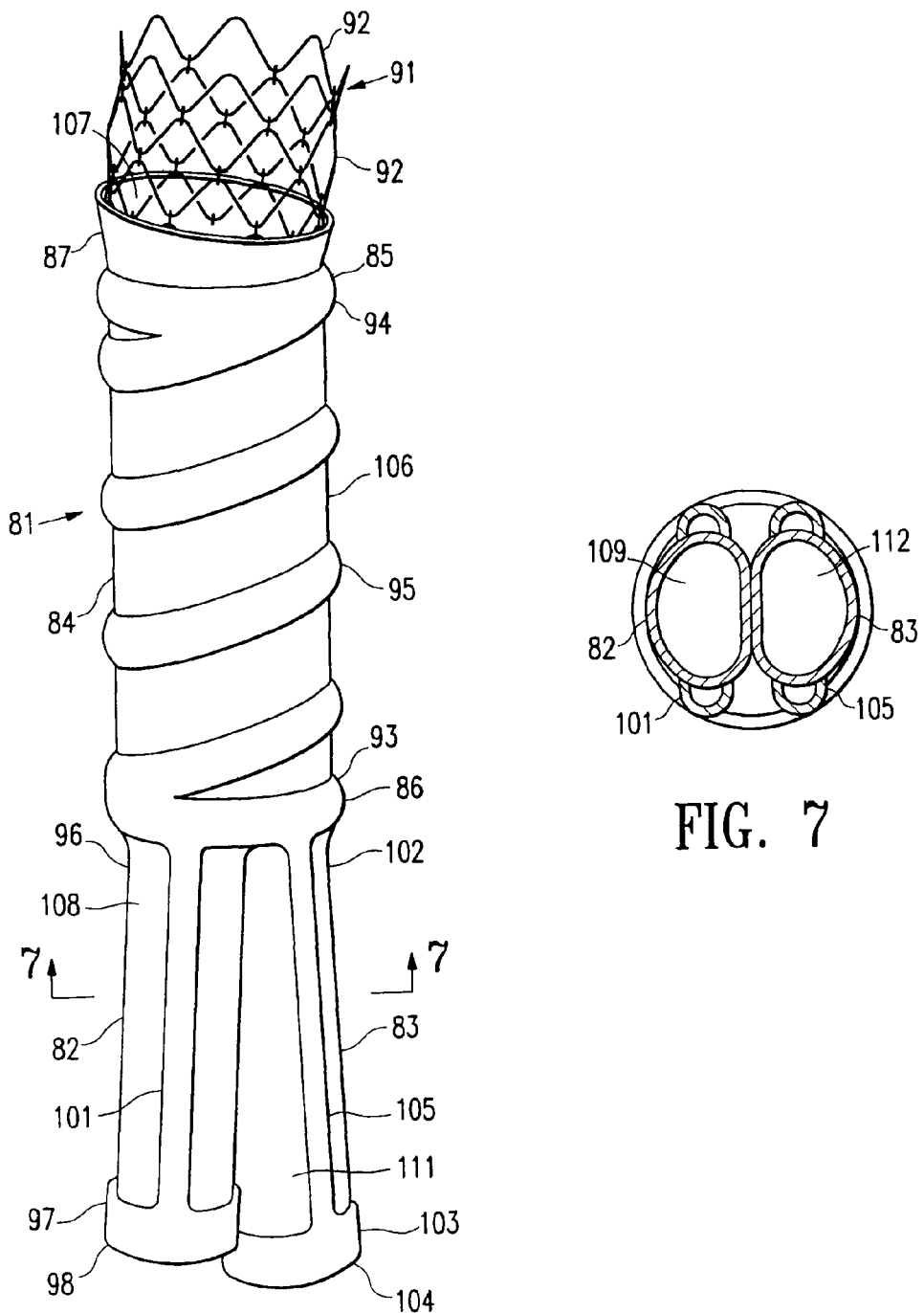
FIG. 6 is a perspective view of a bifurcated endovascular graft having features of the present invention.
FIG. 7 is a transverse cross-sectional view of a bifurcated portion of an endovascular graft taken at 7-7 of FIG. 6.

FIGS. 6 and 7 depict an endovascular graft 81 having features of the invention which has a first bifurcated portion 82 and a second bifurcated portion 83. A main body portion 84 of the graft 81 has a proximal end 85 and a distal end 86 with a proximal neck portion 87 disposed at the proximal end as well as an expansion member 91 which can be formed of expandable rings 92 of a suitable material which have been linked together. At the distal end 86 of the main body portion 84 there is an optional distal inflatable cuff 93 which is connected fluidly to a proximal inflatable cuff 94 by an elongated inflatable channel 95. The distal inflatable cuff 93 may optionally be replaced by a manifold or other suitable structure for fluid connection between the elongated inflatable channel 95 and the first bifurcated portion 82 or the second bifurcated portion 83.

The first bifurcated portion 82 has a proximal end 96 and a distal end 97 with an optional distal inflatable cuff 98 located at the distal end. The distal end of the first bifurcated portion 97 may have an expansion member in conjunction with or in place of the distal inflatable cuff 98. The proximal end 96 of the first bifurcated portion 82 is attached to the distal end 86 of the main body portion 84 of the graft 81. The first bifurcated portion 82 has an optional inflatable elongated channel 101 which fluidly connects the distal inflatable cuff 98 of the first bifurcated portion 82 with the distal inflatable cuff 93 of the main body portion 84. The inflatable elongated channel 101 also provides support for first bifurcated portion 82.

The second bifurcated portion 83 generally has a structure similar to that of the first bifurcated portion 82, with a proximal end 102 and a distal end 103. The distal end 103 has an optional distal inflatable cuff 104. The proximal end 102 of the second bifurcated portion 83 is connected to the distal end 86 of the main body portion 84 of the graft 81. The distal end of the second bifurcated portion 103 may have an expansion member in conjunction with or in place of the distal inflatable cuff 104. The second bifurcated portion 83 has an optional inflatable elongated channel 105 which fluidly connects the distal inflatable cuff 104 of the second bifurcated portion 83 with the distal inflatable cuff 93 of the main body portion 84. The inflatable elongated channel 105 also provides support for the second bifurcated portion 83. The inflatable elongated channel of the first bifurcated portion 101 and inflatable elongated channel of the second bifurcated portion 105 may have a linear configuration as shown, a helical configuration similar to the main body portion 84, or any other suitable configuration. Disposed between the proximal inflatable cuff 94, distal inflatable cuff 93 and elongated inflatable channel 95 of the main body portion 84 of the graft 81 is a thin flexible layer 106 which forms a longitudinal lumen 107 to confine the flow of blood or other bodily fluid therethrough. Disposed between the distal inflatable cuff 98 and the elongated inflatable channel 101 of the first bifurcated portion 82 and the distal inflatable cuff 93 of the main body portion 84 is a first thin flexible layer 108 which forms a. longitudinal lumen 109 which is in fluid communication with the longitudinal lumen 107 of the main body portion 84. The second bifurcated portion may also be formed separate of a main body portion and be joined to the main body portion after percutaneous delivery thereof by docking methods. The first and second bifurcated portions 82 and 83 are generally cylindrical in shape when deployed, although they can conform to the shape of a vessel within which they are deployed, and can have a length from about 1 to about 10 cm. The outside diameter of the distal ends of the first and second bifurcated portions 82 and 83 can be from about 2 to about 30 mm, preferably about 5 to about 20 mm.

A second thin flexible layer 111 is disposed between the distal inflatable cuff 104 and elongated inflatable channel 105 of the second bifurcated portion 83 and the distal inflatable cuff 93 of the main body portion 84. The second thin flexible layer 111 forms a longitudinal lumen 112 which is in fluid communication with the longitudinal lumen 107 of the main body portion 84. The thin flexible layer of the first bifurcated portion surrounds the elongated lumen of the first bifurcated portion. The thin flexible layer of the second bifurcated portion surrounds the elongated lumen of the second bifurcated portion.

FIGS. 8A-8C depict an embodiment of an endovascular graft 121 having features of the invention in various stages of deployment. In FIG. 8A, an inflation catheter 122 is connected to an injection port 123 in a first bifurcated portion 124 of the endovascular graft 121. The injection port 123 is connected to a distal inflatable cuff 125 of the first bifurcated portion 124 and is in fluid communication with a fluid tight chamber 126 therein. The first bifurcated portion 124 and a main body portion 127 have been substantially inflated in FIG. 8A, however, a second bifurcated portion 128 has been prevented from deployment by rupture discs 131 which have been disposed within fluid tight chambers 132 of the elongated inflatable channels 133 of the main body portion 127 which are connected to fluid tight chambers 134 of elongated inflatable channels 135 of the second bifurcated portion 128. In FIG. 8B, the second bifurcated portion 128 has been substantially deployed subsequent to a rupture or bursting of the rupture discs 131 disposed within the fluid tight chambers 132 and 134 of the elongated inflatable channels 133 and 135 which permitted the flow of a pressurized substance therein. FIG. 8C shows the endovascular graft fully deployed and illustrates detachment of a distal end 136 of the inflation catheter 122 from the injection port 123 which is carried out by increasing the pressure within the inflation catheter until a disconnect mechanism 137 is triggered.

Figure 9A:
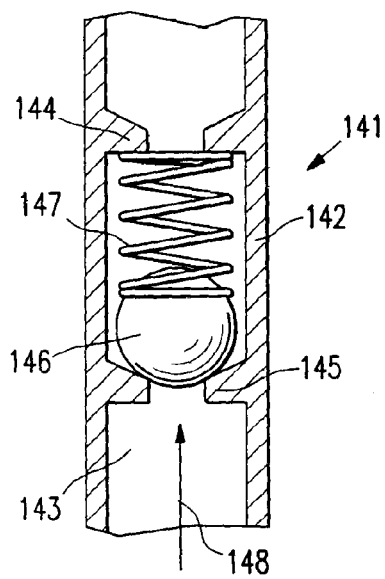
FIG. 9A is an enlarged longitudinal cross sectional view of the valve that could be used to maintain inflation of a fluid tight chamber in the endovascular graft token at 9-9 of FIG. 8A.

FIG. 9A illustrates a longitudinal cross-sectional view taken at 9-9 of FIG. 8A. The one-way inflation valve 141 has an outer wall 142, an inner lumen 143, an annular spring stop 144, an annular ball seal 145, a sealing body 146 and a sealing spring 147. The configuration depicted in FIG. 9A allows for the ingress of an inflation medium in the direction of the arrow 148 while preventing an egress of same once pressure is removed.

Figure 9B:
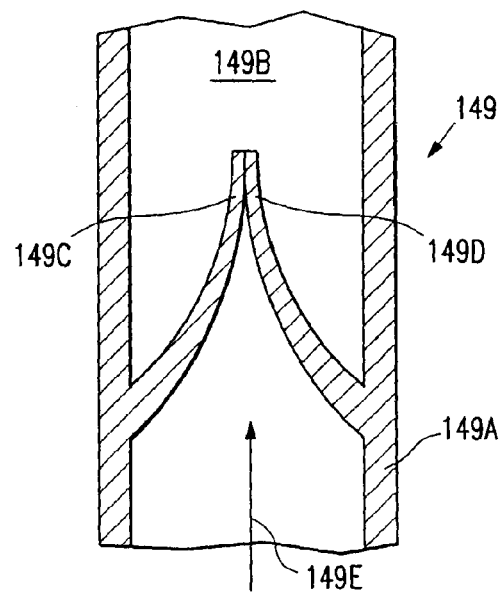
FIG. 9B is an enlarged longitudinal cross sectional view of an alternative seal that could be used to maintain inflation of a fluid tight chamber in the endovascular graft taken at 9-9 of FIG. 8A.

FIG. 9B illustrates an alternative one way valve. The one-way inflation valve 149 has an outer wall 149A, an inner lumen 149B, a first reed valve 149C, and a second reed valve 149D which is fluidly sealed with the first reed valve in a relaxed state. The configuration depicted in FIG. 9B allows for the ingress of an inflation medium in the direction of the arrow 149E while preventing an egress of same once pressure is removed.

Figure 9C:
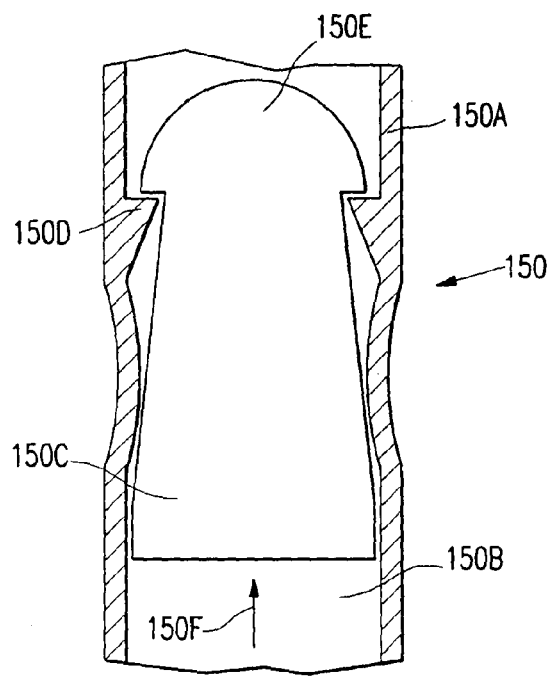
FIG. 9C is an enlarged longitudinal cross sectional view of an alternative sealing plug that could be used to maintain inflation of fluid tight chamber in the endovascular graft taken at 9-9 of FIG. 8A.

FIG. 9C illustrates an alternative seal 150. The seal has an outer wall 150A, an inner lumen 150B, a plug 150C and a sealing surface 150D. The plug 150C has a sealing head 150E which sealingly engages the sealing surface 150D by irreversible deployment by application of force to the plug in the direction of the arrow 150F.

Figure 10:
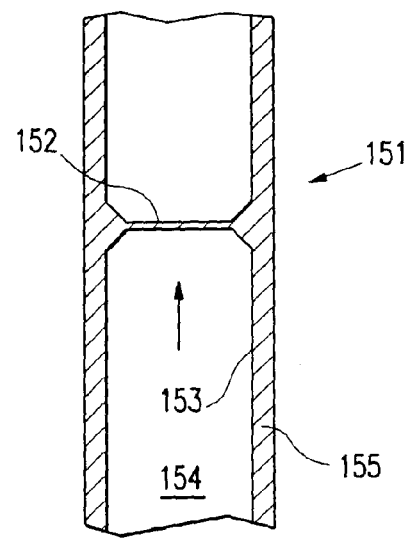
FIG. 10 is an enlarged longitudinal cross sectional view of a rupture disc that could be used to control the inflation sequence of an inflatable endovascular graft taken at 10-10 of FIG. 8C.

FIG. 10 depicts a longitudinal cross-sectional view of a rupture disc 151 taken at 10-10 of FIG. 8C. The rupture disc 151 has a wall member 152 which is sealingly secured to the inside surface 153 of a fluid tight chamber 154. The wall member 152 is configured to fail under pressure prior to the failure of the surrounding wall 155 of the fluid tight chamber 154 under pressure. The rupture disc 151 allows for deployment and inflation of fluid tight chambers other than those which have been sealed by the rupture disc. Once sufficient force or pressure is exerted against the wall 152 of the rupture disc to cause failure, the rupture disc 151 will burst and permit the ingress of an inflation medium and deployment of a portion of an inflatable graft, previously sealed by the rupture disc.

Figure 11:
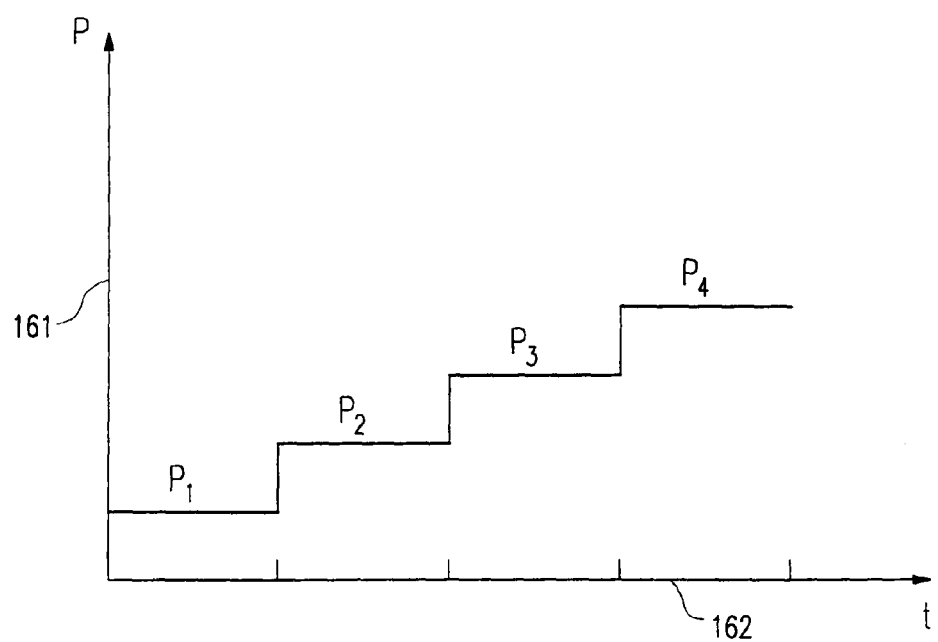
FIG. 11 is a plot of inflation pressure of an inflatable endovascular graft with respect to time for an endovascular graft having features of the present invention including rupture discs which are configured to yield at various predetermined pressures.

FIG. 11 depicts a graphical representation of inflation pressure 161 versus the time 162 at an injection port of an inflatable graft as depicted in FIGS. 8A-8C during the deployment process. $P_1$ represents the inflation pressure at the injection port prior to the rupturing of any rupture discs in the endovascular graft. $P_2$ represents the pressure required to cause failure or bursting of the weakest rupture disc in the endovascular graft after which a portion of the endovascular graft previously sealed by the weakest rupture disc is inflated and deployed. The pressure then increases over time to $P_3$ which is the pressure level required to cause failure or bursting of a second rupture disc. $P_4$ is the pressure level required for triggering a disconnect mechanism at the distal end of the inflation catheter.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A bifurcated endovascular graft system comprising:
a main body portion of biocompatible material having a proximal end and an opposed distal end, the proximal end comprising a proximal neck portion having an open end the main body portion further comprising:
an inflatable cuff permanently secured to the proximal neck portion of the main tubular body portion proximal to the open end of the proximal neck portion; and
a non-inflatable expansion member having a generally cylindrical shape secured to a portion of the proximal neck portion of the main tubular body portion between the inflatable cuff and the end of the proximal neck portion, wherein the non-inflatable expansion member comprises expandable rings formed in a zig-zag pattern, and wherein at least some of the expandable rings formed in the zig-zag pattern of the non-inflatable expansion member extend from and beyond the open end of the proximal neck portion and are configured to exert an outward radial force independent of the main body portion;
a first bifurcated portion having opposed open ends and secured at the distal end of the main body portion; and
a second bifurcated portion having opposed open ends and secured at the distal end of the main body portion.

2. The bifurcated endovascular graft system of claim 1, wherein the inflatable cuff is inflatable with an inflation material to provide an inflated state such that the inflated state conforms to the shape of a body lumen.

3. The bifurcated endovascular graft system of claim 1, wherein at least one of the first and the second bifurcated portions are securable to distal end of the main body portion after percutaneous delivery thereof.

4. The bifurcated endovascular graft system of claim 1, wherein the first and the second bifurcated portions are securable to distal end of the main body portion after percutaneous delivery thereof.

5. The bifurcated endovascular graft system of claim 1, wherein at least one of the first and the second bifurcated portions further comprise an expansion member.

6. The bifurcated endovascular graft system of claim 1, wherein at least one of the first and the second bifurcated portions further comprise an inflatable channel.

7. The bifurcated endovascular graft system of claim 1, wherein the biocompatible material of the main body portion comprises a polymeric material selected from the group consisting of polyvinylchloride (PVC), polyurethane, polyethylene and polyethylene terephthalate (PET).

8. The bifurcated endovascular graft system of claim 1, wherein the biocompatible material of the main body portion comprises a fluoropolymer.

9. The bifurcated endovascular graft system of claim 8, wherein the fluoropolymer comprises polytetrafluoroethylene (PTFE) or expanded polytetrafluoroethylene (ePTFE).

10. The bifurcated endovascular graft system of claim 1, wherein the non-inflatable expansion member is a self-expanding member.

11. The bifurcated endovascular graft system of claim 1, wherein the non-inflatable expansion member comprises a shape memory alloy.

12. The bifurcated endovascular graft system of claim 11, wherein the shape memory alloy comprises nitinol.

13. The bifurcated endovascular graft system of claim 1, the first and the second bifurcated portions each has a longitudinal lumen that is in fluid communication with a longitudinal lumen of the main body portion.

14. The bifurcated endovascular graft system of claim 13, wherein the first bifurcated portion and the second bifurcated portion each further comprise an inflatable channel.

15. The bifurcated endovascular graft system of claim 13, wherein the first bifurcated portion and the second bifurcated portion each further comprise an inflatable cuff.

* * * * *